(12) United States Patent
Fukazu (10) Patent No.: US 11,769,588 B2
(45) Date of Patent: Sep. 26, 2023

(54) RADIOGRAPHY CONTROL APPARATUS, RADIOGRAPHY SYSTEM, DISPLAY CONTROL METHOD, AND STORAGE MEDIUM

(71) Applicant: Konica Minolta, Inc., Tokyo (JP)

(72) Inventor: Kosuke Fukazu, Hino (JP)

(73) Assignee: KONICA MINOLTA, INC., Tokyo (JP)

(*) Notice: Subject to any disclaimer, the term of this patent is extended or adjusted under 35 U.S.C. 154(b) by 117 days.

(21) Appl. No.: 17/132,051

(22) Filed: Dec. 23, 2020

(65) Prior Publication Data

US 2021/0241896 A1  Aug. 5, 2021

(30) Foreign Application Priority Data

Jan. 30, 2020 (JP) .................. 2020-013406

(51) Int. Cl.
*G16H 40/63* (2018.01)
*G06F 3/0482* (2013.01)
(Continued)

(52) U.S. Cl.
CPC ............. *G16H 40/63* (2018.01); *A61B 6/463* (2013.01); *A61B 6/465* (2013.01); *A61B 6/469* (2013.01); *A61B 6/54* (2013.01); *G06F 3/0482* (2013.01); *G06F 3/04817* (2013.01); *G16H 15/00* (2018.01); *G16H 30/20* (2018.01);
(Continued)

(58) Field of Classification Search
CPC ......... A61B 6/463; A61B 6/465; A61B 6/469; A61B 6/54; G16H 15/00; G16H 30/20; G16H 30/40; G16H 40/63; G16H 70/20; G06F 3/04817; G06F 3/0482; G06F 2203/04803
See application file for complete search history.

(56) References Cited

U.S. PATENT DOCUMENTS

2005/0259116 A1* 11/2005 Araoka ................... G06T 19/00
345/619
2008/0126982 A1* 5/2008 Sadikali ................. G16H 50/70
715/810
(Continued)

FOREIGN PATENT DOCUMENTS

JP 2006-263223 A 10/2006
JP 2010-110433 A 5/2010
JP 2015-084938 A 5/2015

OTHER PUBLICATIONS

Office Action dated Jul. 18, 2023 for corresponding Japanese Application No. 2020-013406, with English translation.

*Primary Examiner* — Dani Fox
*Assistant Examiner* — Soorena Kefayati
(74) *Attorney, Agent, or Firm* — LUCAS & MERCANTI, LLP (57) ABSTRACT

A radiography control apparatus includes a display that includes a display screen and a hardware processor. In causing the display screen to display a list of information on an examination that is set for a patient and that relates to taking a radiographic image, the hardware processor causes the display screen to display, in a display area, an imaging item that is included in the examination and categorized into a category based on a set categorization criterion, separating the imaging item by the category.

15 Claims, 8 Drawing Sheets

(51) Int. Cl.
*G06F 3/04817* (2022.01)
*G16H 15/00* (2018.01)
*G16H 30/20* (2018.01)
*G16H 70/20* (2018.01)
*A61B 6/00* (2006.01)
*G16H 30/40* (2018.01)

(52) U.S. Cl.
CPC ............ *G16H 30/40* (2018.01); *G16H 70/20* (2018.01); *G06F 2203/04803* (2013.01)

(56) References Cited

U.S. PATENT DOCUMENTS

| | | | |
|---|---|---|---|
| 2010/0272343 A1* | 10/2010 | Abe | G16H 40/63 382/132 |
| 2011/0311026 A1* | 12/2011 | Lalena | G16H 40/63 378/98.5 |
| 2013/0038738 A1* | 2/2013 | Ando | A61B 6/585 348/E5.085 |
| 2013/0088512 A1* | 4/2013 | Suzuki | G16H 10/60 345/629 |
| 2013/0298082 A1* | 11/2013 | Soffer | G06F 3/0482 715/835 |
| 2014/0119514 A1* | 5/2014 | Miyazawa | G16H 40/63 378/98 |
| 2014/0285525 A1* | 9/2014 | Okusu | G06F 3/0346 345/659 |
| 2015/0117607 A1* | 4/2015 | Hayashi | A61B 6/465 715/767 |
| 2015/0265233 A1* | 9/2015 | Aoyagi | G06F 3/1446 345/635 |
| 2015/0272526 A1* | 10/2015 | Hikosaka | A61B 6/54 378/95 |
| 2016/0073987 A1* | 3/2016 | Ohashi | A61B 6/508 345/173 |
| 2016/0078596 A1* | 3/2016 | Ohashi | A61B 6/566 378/62 |
| 2016/0081642 A1* | 3/2016 | Okusu | A61B 6/4452 715/709 |
| 2016/0081650 A1* | 3/2016 | Okusu | A61B 6/566 715/826 |
| 2016/0133012 A1* | 5/2016 | Miyazawa | G06T 7/0012 382/132 |
| 2016/0166227 A1* | 6/2016 | Tanaka | A61B 6/563 382/132 |
| 2016/0196045 A1* | 7/2016 | Abe | A61B 6/5294 715/765 |
| 2016/0199015 A1* | 7/2016 | Li | H04N 13/398 348/51 |
| 2016/0213347 A1* | 7/2016 | Kawanishi | A61B 6/465 |
| 2016/0228081 A1* | 8/2016 | Inoue | A61B 6/465 |
| 2016/0228087 A1* | 8/2016 | Oda | A61B 6/5211 |
| 2016/0310099 A1* | 10/2016 | Hamano | A61B 6/563 |
| 2017/0042009 A1* | 2/2017 | Nishijima | A61B 6/465 |
| 2017/0069084 A1* | 3/2017 | Kubo | G06V 10/26 |
| 2017/0091413 A1* | 3/2017 | Kondo | G16H 50/70 |
| 2017/0238892 A1* | 8/2017 | Taneda | A61B 6/467 |
| 2017/0303884 A1* | 10/2017 | Takasawa | A61B 6/467 |
| 2017/0367669 A1* | 12/2017 | Shimada | A61B 6/465 |
| 2018/0107788 A1* | 4/2018 | Abe | G16H 30/20 |
| 2018/0125441 A1* | 5/2018 | Arima | G16H 30/20 |
| 2018/0218785 A1* | 8/2018 | Sugiyama | A61B 6/037 |
| 2019/0028657 A1* | 1/2019 | Katsushi | H04N 5/30 |
| 2019/0279408 A1* | 9/2019 | Hirakawa | G06T 11/60 |
| 2019/0348156 A1* | 11/2019 | Fram | G16H 30/20 |
| 2020/0141882 A1* | 5/2020 | Kawanishi | A61B 6/563 |
| 2020/0323504 A1* | 10/2020 | Okabe | A61B 6/463 |

* cited by examiner

RADIOGRAPHY CONTROL APPARATUS, RADIOGRAPHY SYSTEM, DISPLAY CONTROL METHOD, AND STORAGE MEDIUM

CROSS-REFERENCE TO RELATED APPLICATIONS

The entire disclosure of Japanese Patent Application No 2020-13406, filed on Jan. 30, 2020 is incorporated herein by reference in its entirety.

BACKGROUND

Technological Field

The present disclosure relates to a radiography control apparatus, a radiography system, a display control method, and a storage medium.

Description of Related Art

A known radiography system performs examinations by irradiating an examination target and taking radiographic images that show how much radiation has penetrated the target. In the radiography system, a radiography control apparatus controls a radiographic-image taking apparatus (es) that takes radiographic images. When receiving an examination appointment, the radiography control apparatus may set multiple imaging items (instances) for the imaging target (e.g., patient) and perform radiography for the respective imaging items. Each imaging item determines a radiographic-image taking apparatus(es), a body part to be imaged, and imaging conditions, for example. Examination appointments may not be made by one time by a single doctor/medical department but may be made through several requests or by different doctors/departments at close timings.

To deal with such circumstances, JP2006-263223A discloses a technology to reduce time and effort of patients and radiographers. According to the technology, an imaging control apparatus displays, on its display screen, a list of imaging items in requested examinations, and a radiographer is allowed to determine appropriate examination orders and manage the imaging items as a group of examinations.

However, an examiner may not recognize which examination is performed in the list. The examiner may find it difficult to recognize relationship between taken images or may tend to overlook the imaging menu.

Objects of the present disclosure include providing a radiography control apparatus, a radiography system, a display control method, and a storage medium that allow examiners to visually recognize examination information more efficiently and securely.

To achieve at least one of the abovementioned objects, according to an aspect of the present invention, a radiography control apparatus includes: a display that includes a display screen; and a hardware processor, wherein the hardware processor causes the display screen to display a list of information on an examination that is set for a patient and that relates to taking a radiographic image, and causes the display screen to display, in a display area, an imaging item that is included in the examination and categorized into a category based on a set categorization criterion, separating the imaging item by the category.

To achieve at least one of the abovementioned objects, according to another aspect of the present invention, a display control method for displaying, on a display, information on an examination that relates to taking a radiographic image includes: item displaying that is, in causing a display screen of the display to display a list of the information on the examination that is set for a patient, causing the display screen to display, in a display area, an imaging item that is included in the examination and categorized into a category based on a set categorization criterion such that the imaging item is separated by the category.

To achieve at least one of the abovementioned objects, according to another aspect of the present invention, a non-transitory computer readable storage medium stores a program that causes a computer including a display with a display screen to display, on the display screen, a list of information on an examination that is set for a patient and that relates to taking a radiographic image, wherein the computer displays, in a display area, an imaging item that is included in the examination and categorized into a category based on a set categorization criterion, separating the imaging item by the category.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention are described referring to the drawings. However, the invention is not limited to the disclosed embodiments.

Figure 1:
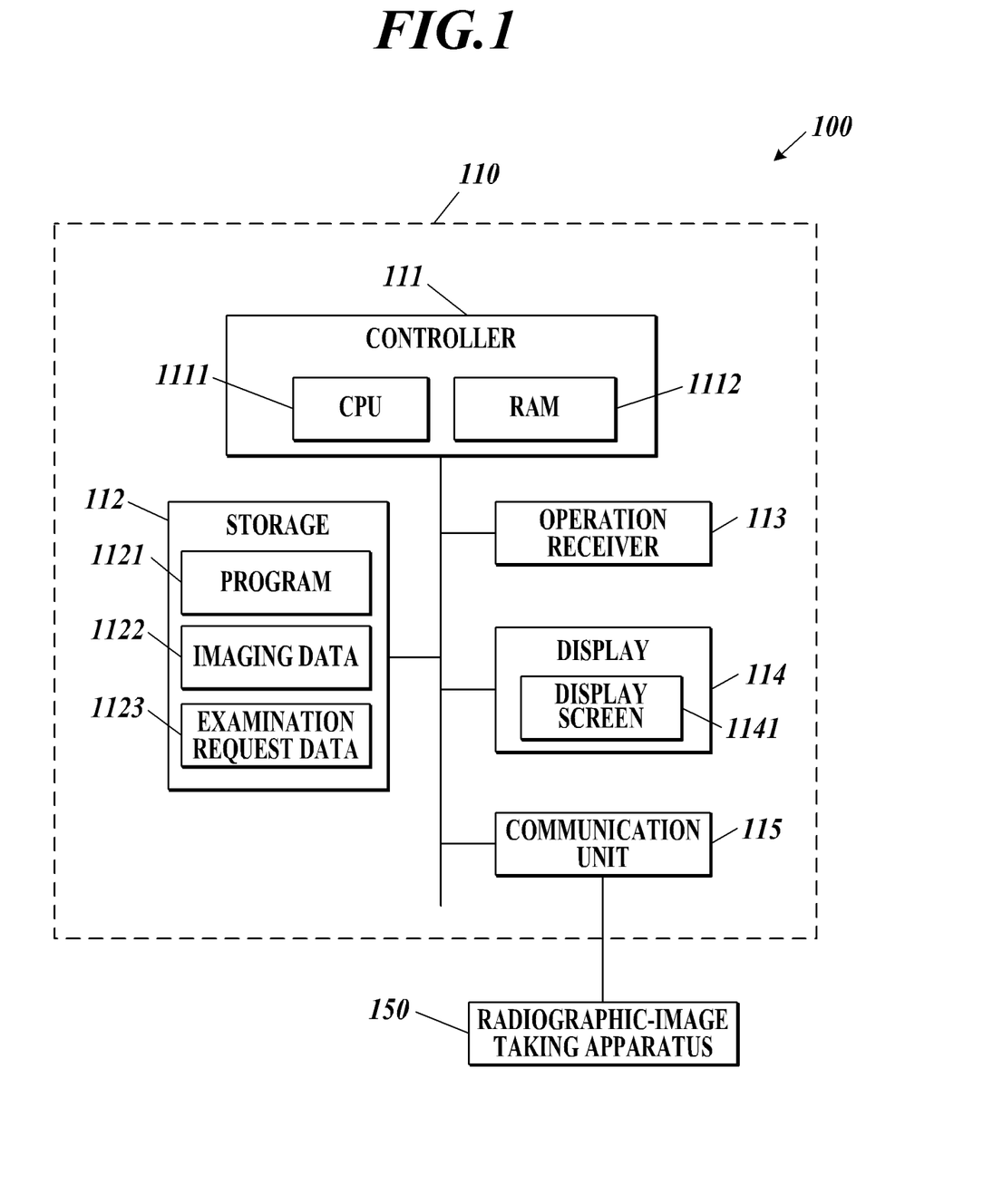
FIG. 1 is a block diagram showing functional components of a radiography system.

FIG. 1 is a block diagram showing functional components of a radiography system 100 in this embodiment.

The radiography system 100 includes a radiographic-image taking apparatus 150 and a radiography control apparatus 110.

The radiography control apparatus 110 includes a controller 111 (hardware processor), a storage 112, an operation receiver 113, a display 114, and a communication unit 115. The radiography control apparatus 110 may be a computer, such as a normal personal computer (PC).

The controller 111 centrally controls operations of the components of the radiography control apparatus 110. The controller 111 is a hardware processor that includes a central processing unit (CPU) 1111 and a random access memory (RAM) 1112. The CPU 1111 performs arithmetic processing to perform various control operations. The RAM 1112 provides a working memory space for the CPU 1111 and stores temporary data.

The storage 112 is a nonvolatile memory and includes a hard disk drive (HDD) and/or a flash memory. The storage 112 stores programs 1121, imaging data 1122, and examination request data 1123.

The programs 1121 include various control programs, such as a program for the display control process to be described below, according to the display control method in this embodiment. These control programs are read and performed by the CPU 1111.

The imaging data 1122 includes data of images taken by the radiographic-image taking apparatus 150 and auxiliary information data that is associated with the data of taken images. The auxiliary information data includes, for example, an examination ID, a patient ID, the name, the age, and the sex of the patient, the imaged date, and the imaging conditions.

The examination request data 1123 is data on examination requests with radiography. The examination requests are received from the hospital information systems (HIS) and/or the radiology information systems (RIS), for example. The examination request data 1123 includes, for example, information on the examination ID, the patient ID, the name, the age, and the sex of the patient, the appointed date for radiography, the department that requested the examination, and the imaging part.

The operation receiver 113 receives input operations from outside, such as operations performed by a user of the radiography control apparatus 110 (e.g., examiner), and outputs input signals to the controller 111. The operation receiver 113 includes, for example, all or part of the following: a touchscreen superposed on the display 114; a keyboard that receives operations performed with keys; a pointing device, such as a mouse; and various switching buttons. Part of these operation receiving devices may be connected according to the universal serial bus (USB) via an I/O interface 1153, which is described below. The operation receiver 113 may further include a microphone to detect sounds, such as voice of the user. The controller 111 may recognize the content of the detected voice to determine the content of operation.

The display 114 includes a display screen 1141 and displays various contents on the display screen 1141 under the control of the controller 111. The display screen 1141 is, for example, a color liquid crystal display screen but is not limited thereto. The display screen 114 may display contents of imaging data, or more specifically, the data of taken images and the auxiliary information data. The display 114 may further include a notifying lump and/or an indicator with the light-emitting diode (LED).

The communication unit 115 controls communication and data exchange with external apparatuses and peripherals. The communication unit 115 performs communication by connecting to the local area network (LAN) via a wired or wireless communication, for example. The apparatuses to be connected for communication include the radiographic-image taking apparatus 150. The communication unit 115 includes the I/O interface and exchanges data with the peripherals via the USB connection or any other connections. The peripherals to be connected to the I/O interface 1153 may include: operation devices, such as the above-mentioned pointing device; a storage device, such as an external HDD and a flash memory; and a disk drive for reading and writing on a storage medium (particularly for recording and outputting imaging data), such as a DVD and a Blu-ray disk (registered trademark).

Next, the radiography control screen that is displayed on the radiography control apparatus 110 is described.

Figure 2:
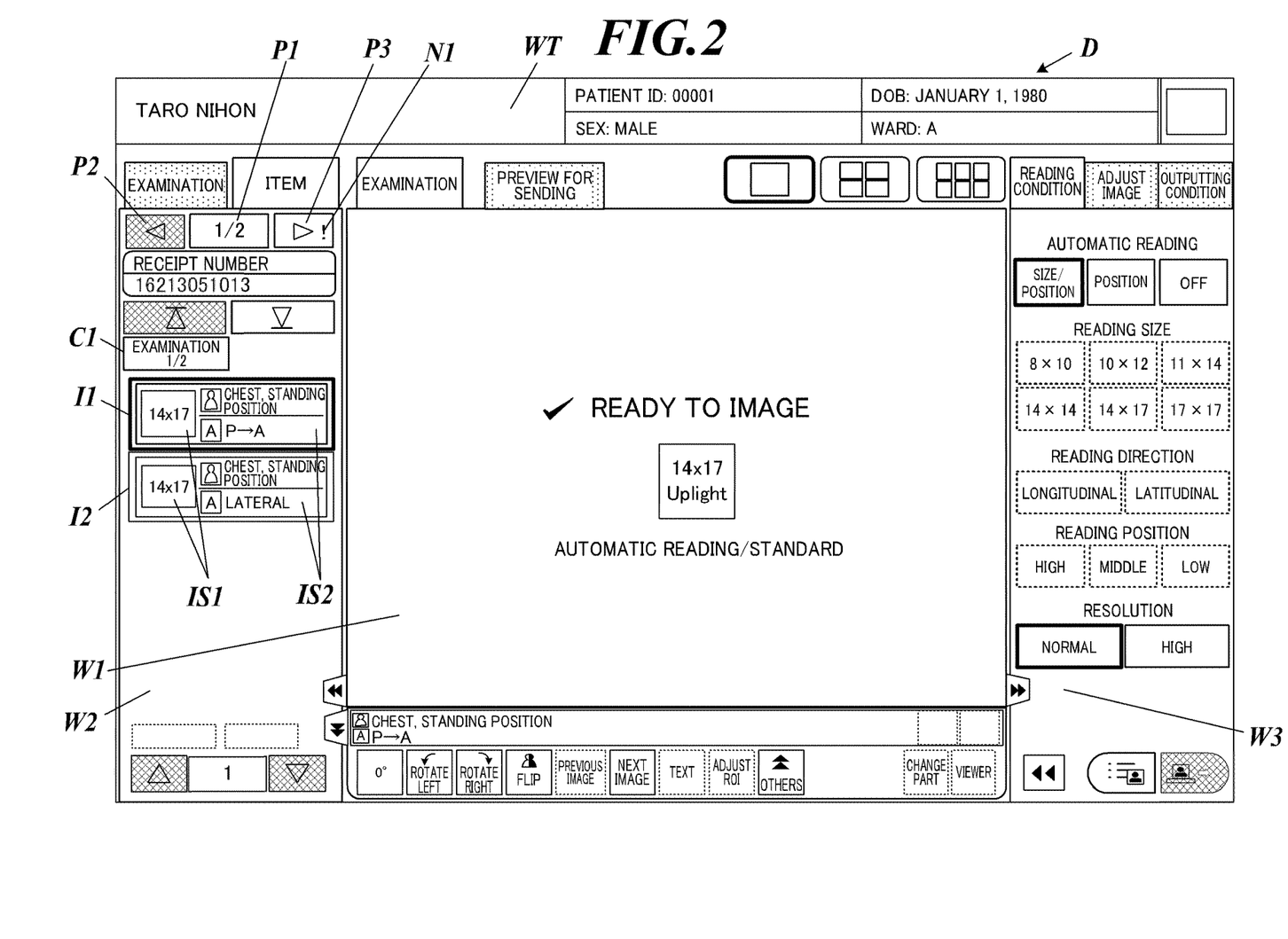
FIG. 2 shows an example of a radiography control screen.

FIG. 2 shows an example of the radiography control screen.

The radiography control screen D includes a title section WT in the upper part. The title section WT shows personal information, such as the name of the patient, to identify the patient as an imaging target. The radiography control screen D further includes, at its center, a preview section W1 for previewing the data of taken images. At the right of the preview section W1, a setting section W3 is provided for setting conditions of reading, adjusting, and outputting the taken images. At the left of the preview section W1, a list section W2 is provided for showing a list of examination information. The examination information is set for the identified patient and relates to taking a radiographic image(s) of the patient. The examination information includes one or more imaging items. Each imaging item shows a combination of one or more imaging parts and imaging conditions specified in the examination.

In the list section W2 in FIG. 2, two imaging items I1, I2 are set and shown next to each other. These imaging items are set for the examination 1 and shown together with an icon C1 that indicates the examination 1 as a category.

In this embodiment, all the imaging items are categorized into categories based on a set categorization criterion. In the list section W2, the categorized imaging items are separated by the category and displayed.

The imaging items I1, I2 each include a thumbnail display section IS1 and an information display section IS2. The information display section IS2 shows imaging information, such as the imaging part(s) and the summary of imaging conditions. When an imaging item is undone (i.e., radiography has not been performed yet for the imaging item), the thumbnail display section IS1 shows the imaging size as a predetermined indication. This allows the user to recognize whether or not radiography has been performed for the imaging item. In FIG. 2, the imaging item I1 is selected and highlighted with a thick-line frame. The imaging item I1 is associated with the preview section W1. The setting for the selected imaging item I1 is done on the setting section W3. Herein, the position and size of the region to be examined are set to be automatically read based on a taken image having the standard resolution. When the automatic reading is not set, the size, direction, and position of reading can be set manually.

The list section W2 includes a page section P1. The page section P1 in FIG. 2 indicates that the page 1 among two pages in total is shown. Herein, the icon P2 for switching to the previous page is not selectable. The icon P3 for switching to the next page has "!" as a notification icon N1. The notification icon N1 (predetermined indication) indicates that the page that is not displayed in the list section W2 has an undone imaging item for which radiography has not been performed yet. With the notification icon N1, the radiographer can avoid failing to perform radiography. The notification icon N1 may be shown on the icon P3 when an undone imaging item(s) is present among the imaging items on the third page or the page thereafter, which are displayed by selecting the icon P3 multiple times, as well as when an undone imaging item(s) is present among imaging items on the second page, which is displayed by selecting the icon P3 once.

The radiography control apparatus 110 displays the imaging items in the list section W2 such that the imaging items are separated based on the set categories. The categories in FIG. 2 are examination requests. The icon C1 indicates that the first examination is shown among two examination requests having been received. Together with the icon C1, two imaging items I1, I2 are displayed. When the icon P3 is selected, the imaging item(s) of the second examination among the two examinations is displayed. Thus, all the imaging items included in multiple examination requests for a single patient can be altogether displayed as a list. These imaging items are separately displayed based on categories. This allows the user to check the imaging items in an organized manner. The imaging items may be appropriately divided into pages for display. For example, the imaging items may be divided by the category such that the imaging items in the same category are displayed on the same page, not on multiple pages. The items being displayed may be switched by categories.

Figure 3A:
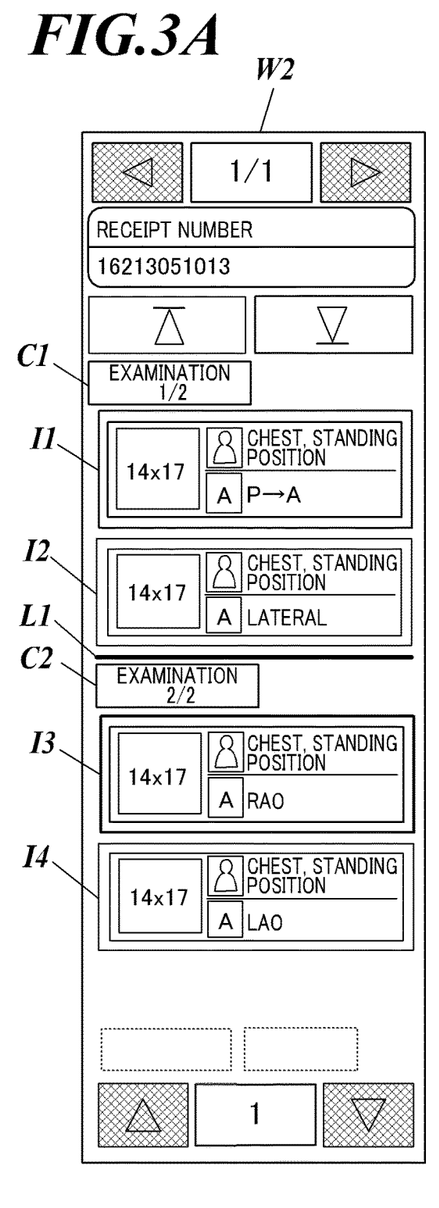
FIGS. 3A, 3B show examples of how to separate categories in a list.
Figure 3B:
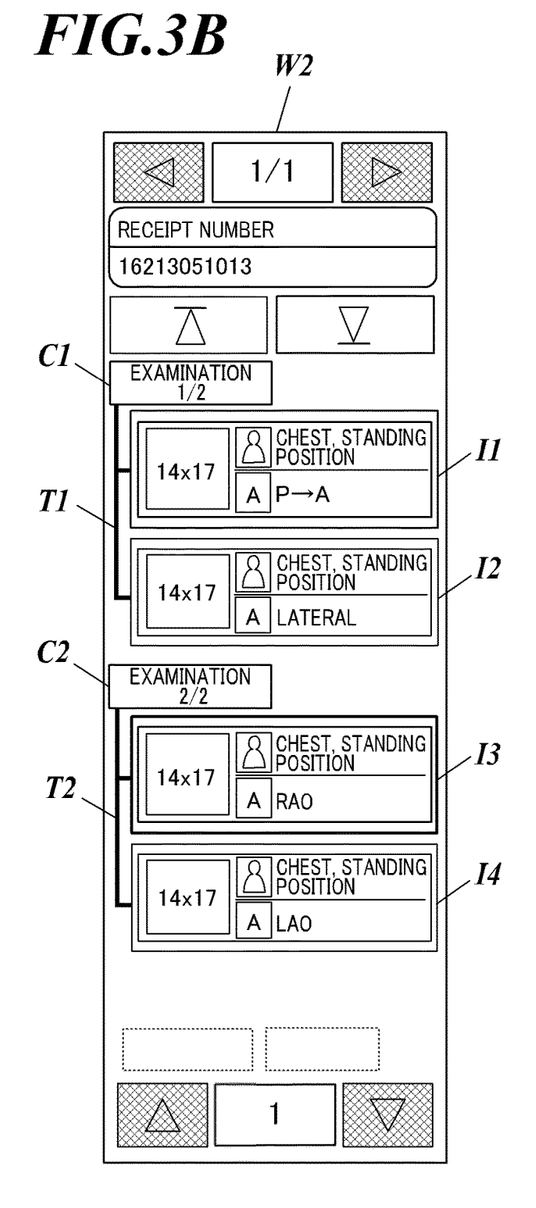
Figure 4A:
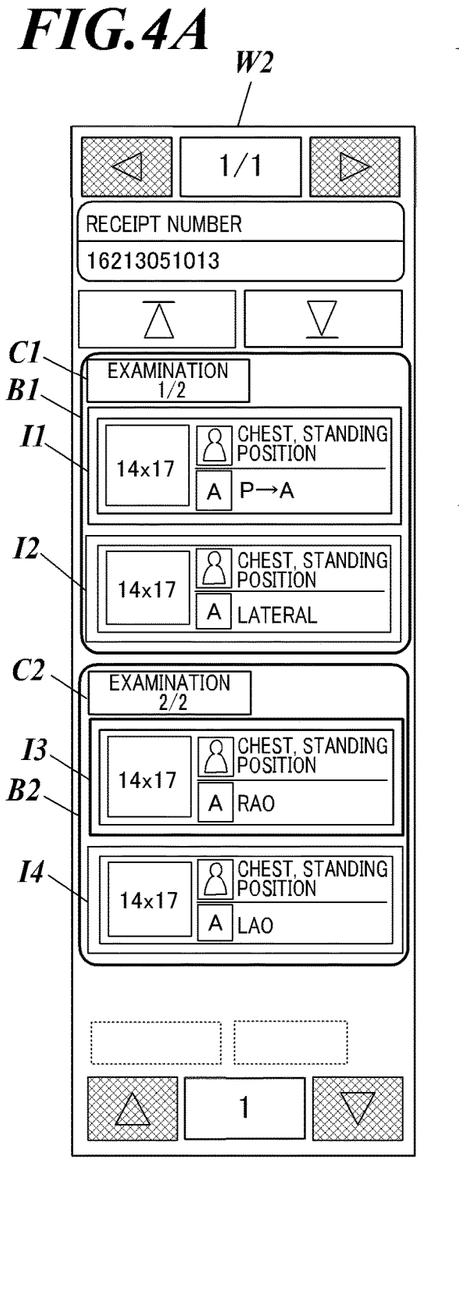
FIGS. 4A, 4B show examples of how to separate categories in the list.
Figure 4B:
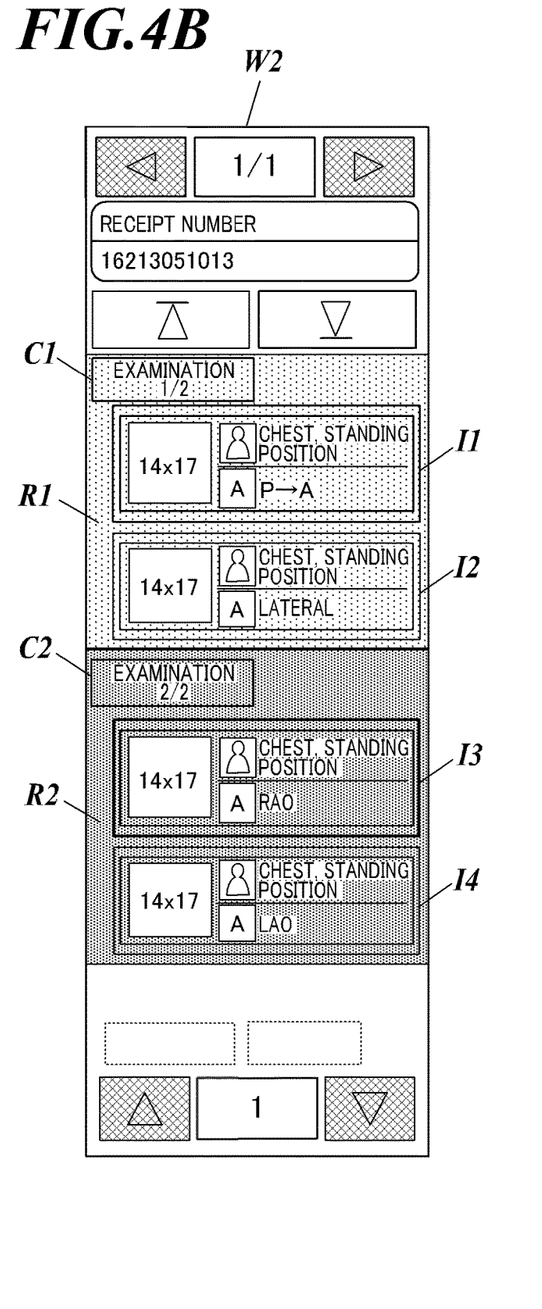

FIG. 3 and FIG. 4 show other examples of separating categories in the list section W2.

FIG. 3A shows a second example of the list section W2. Herein, two examination requests are displayed together in the list section W2. These examination requests are separated as different categories by a level separating line L1 (predetermined separating icon). Each of the categories has a region for displaying the imaging items. At the top of each region, an icon C1/C2 that indicates the corresponding category is shown. Under the icon C1, imaging items I1, I2 are displayed in the imaging-item display region of the examination 1. Under the icon C2, the imaging items I3, I4 are displayed in the imaging-item display region of the examination 2.

FIG. 3B shows a third example of the list section W2. Herein, trees T1, T2 are used instead of the separating line L1. The trees T1, T2 connect the imaging items to the respective category icons C1, C2 to which the imaging items belong. More specifically, the tree T1 connects the imaging items I1, I2 to the category icon C1, and the tree T2 connects the imaging items I3, I4 to the category icon C2. The trees may have other forms, such as straight or curved lines.

FIG. 4A shows a fourth example of the list section W2. Herein, the imaging items that belong to the same category are grouped in a region (subarea) defined by the borderline B1/B2 and are thereby separated from the imaging items that belong to the other category. The borderline B1 encloses the icon C1 and the imaging items I1, I2 that belong to the category of the examination 1. The borderline B2 encloses the icon C2 and the imaging items I3, I4 that belong to the category of the examination 2.

FIG. 4B shows a fifth example of the list section W2. Herein, the imaging items that belong to the same category are placed in the region (subarea) of the same background color. The icon C1 and the imaging items I1, I2 that belong to the category of the examination 1 are placed in the region R1 having a predetermined background color. The icon C2 and the imaging items I3, I4 that belong to the category of the examination 2 are placed in the region R2 having a background color different from the background color of the region R1. Not only the backgrounds but also the category icons may have different colors. The backgrounds and the category icons may be set to have specific colors associated with categories. The colors may be set by the user. Displaying the color-coded backgrounds and/or category icons allows the user (e.g., radiographer) to recognize the categorization criterion quickly and intuitively.

By separately displaying imaging items based on categories as described above, different categories can be displayed in the same display region. More imaging items can therefore be displayed as a list with less switching operations. When all the imaging items cannot be displayed in one page of the list section W2, the remaining imaging items may be carried over to the next page(s) on a category basis. Alternatively, all the imaging items may be included in one page so as to be sequentially displayed as the page is scrolled. When undone imaging items are present in the not-displayed region, a notification may be shown on the scroll bar.

Figure 5A:
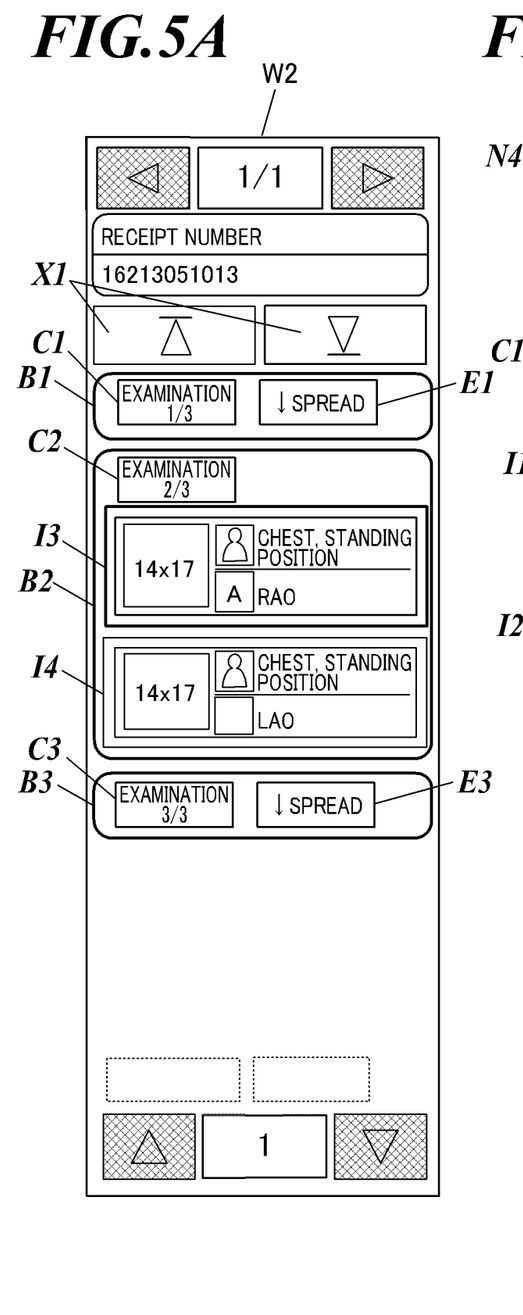
FIGS. 5A, 5B show examples of how to display the list.
Figure 5B:
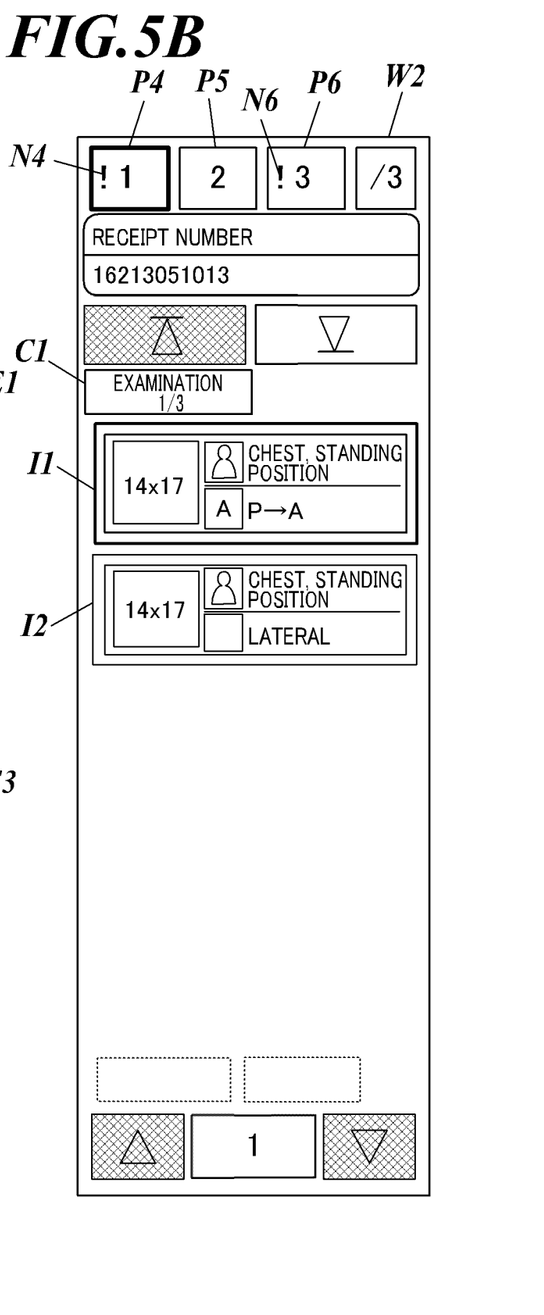

FIGS. 5A, 5B show other examples of the list section W2.

The list section W2 in FIG. 5A shows all the three categories on the same display screen. Among the categories, only the category of the examination 2 is spread to show the imaging items I3, I4. Thus, the list section W2 may be set to display many categories when all the imaging items cannot be displayed in one page. The category for which all the imaging items are displayed is switched when the spreading icon E1/E3 is selected. The category for which all the imaging items are displayed may not be alternately selected. The user may determine category by category whether or not to spread all the imaging items. The category for which all the imaging items are spread and displayed may have an icon for undoing the spreading.

An imaging item may not be directly selected. Assume that the imaging item I3 is currently selected and that an operation is performed to move to the imaging item I2 that is immediately before the imaging item I3 or the imaging item I1 that is at the top in the arrangement order or the predetermined imaging order (e.g., operation of selecting the switching icon X1 or input operation with arrow keys on the keyboard). In such a case, the display contents may be automatically changed such that the category that includes the selected imaging item is spread to show its imaging items.

The list section W2 in FIG. 5B shows icons P4 to P6 each of which indicates the page number to be selected. The user can directly select and move to a page instead of switching the pages one by one by selecting the arrow icons P2, P3. In FIG. 5B, a notification icon N4 is shown on the icon P4 for the page 1, and a notification icon N6 is shown on the icon P6 for the page 3. The notification icons N4, N6 indicate that undone imaging items are present on the pages 1, 3. The display content can be switched directly from the imaging items of the currently selected page 1 to the imaging items of the page 3. Instead of showing icons that indicate all the page numbers in the list section W2, all the page numbers may be shown on a pull-down menu or a pop-up window only in selecting or switching the pages. The selection may be made in response to the operation received by the operation receiver 113.

The categorization criterion for separating imaging items can be changed.

Figure 6A:
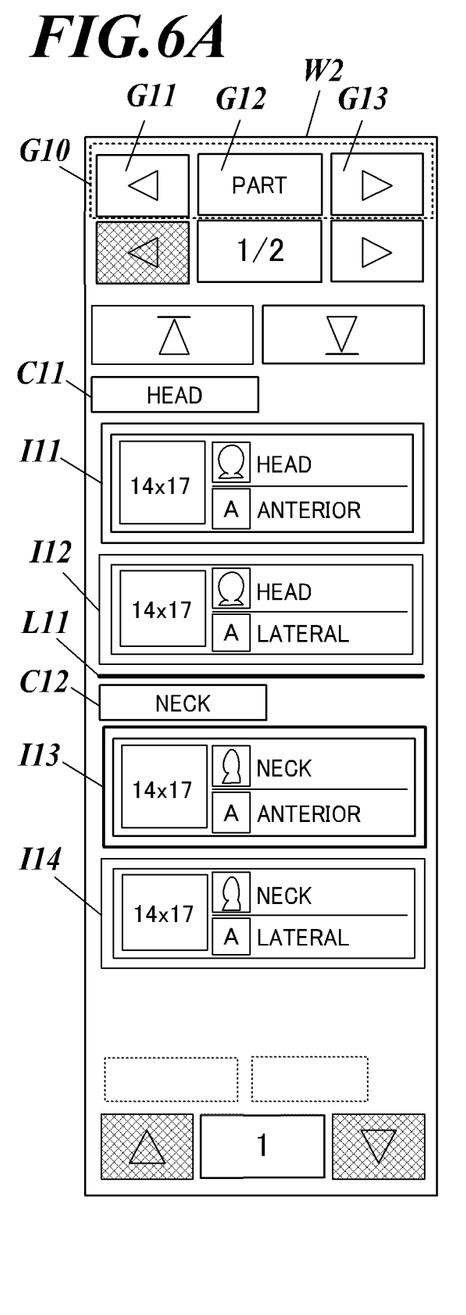
FIGS. 6A, 6B show examples of categorization.
Figure 6B:
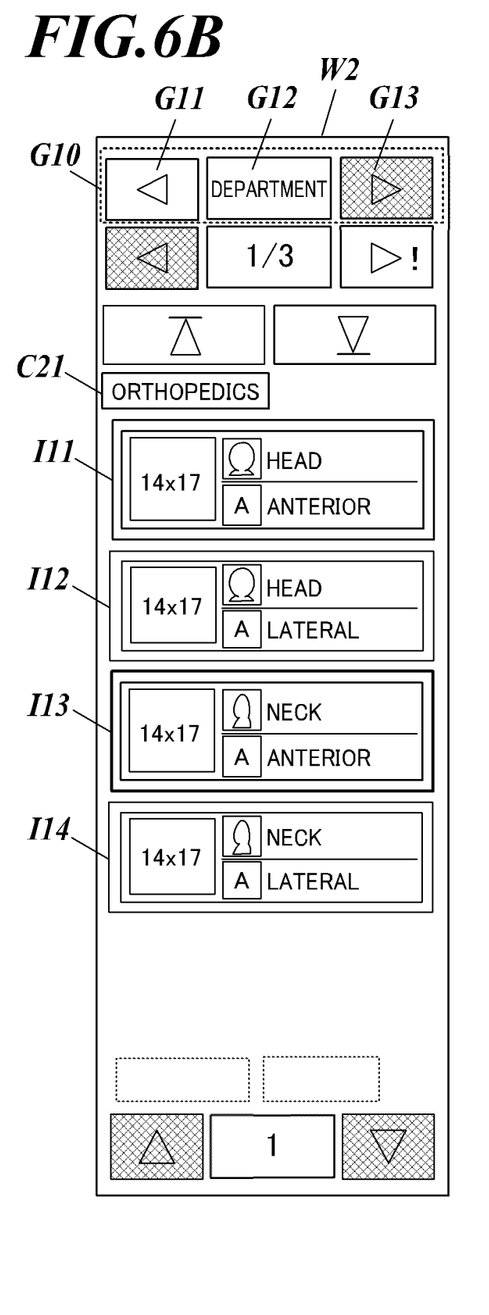

FIGS. 6A, 6B show other examples of categorization.

In the list section W2 in FIG. 6A, the categorization criterion is set to imaging parts. The categories "head" and "neck" are set and shown in the respective category icons C11, C12 Imaging items I11, I12 that belong to the category "head" are shown next to the icon C11 Imaging items I13, I14 that belong to the category "neck" are shown next to the icon C12. These categories are separated by the separating line L11.

Multiple categorization criteria may be set beforehand. Herein, the selecting section G10 is shown at the top of the list section W2. In setting the categorization criterion, the categorization criteria may be switched in a predetermined order when the operation receiver 113 receives the operation (input operation) of selecting the arrow icons G11, G13. Alternatively, a list of selectable criteria may be shown in a pull-down menu or a pop-up window when the display icon G12 that indicates the currently selected categorization criterion is selected. The user is thus allowed to directly select a criterion in the list.

In the list section W2 in FIG. 6B, the categorization criterion is set to medical departments who requested examinations. FIG. 6B shows the first page of the list. The list section W2 shows the category icon C21 that indicates the orthopedics department and imaging items I11 to I14 that have been requested by the orthopedics department.

Other categorization criteria may be, for example, (i) image-taking apparatuses or, in particular, radiation detectors, (ii) postures of patients (standing/lying and the direction thereof), (iii) timings when examinations are requested, and (iv) appointed dates for examinations. The multiple categorization criteria having been set may have different background/foreground colors and fonts.

Multiple examination requests for a single patient may include multiple imaging items that have the same imaging content, such as the same imaging part or the same imaging conditions. In such a case, a radiographer does not have to perform the same radiography several times for the individual imaging items, unless radiography at different timings is requested (e g, examinations of performing radiography at different timings are requested to observe time-series changes). When radiography is performed once for one imaging item, the radiography is considered to be performed for all the other imaging items having the same imaging content, and the data of taken images may be set as common data for all the imaging items. When a taken image is subject to different reading operations or different types of image processing, departments may individually select the image and do the reading setting. On the other hand, when the imaging items have the same imaging part and the same imaging conditions, the imaging items do not have to be dealt individually. When these imaging items are categorized based on imaging parts and separately displayed, each category needs to show only one among the imaging items having the same content.

Figure 7A:
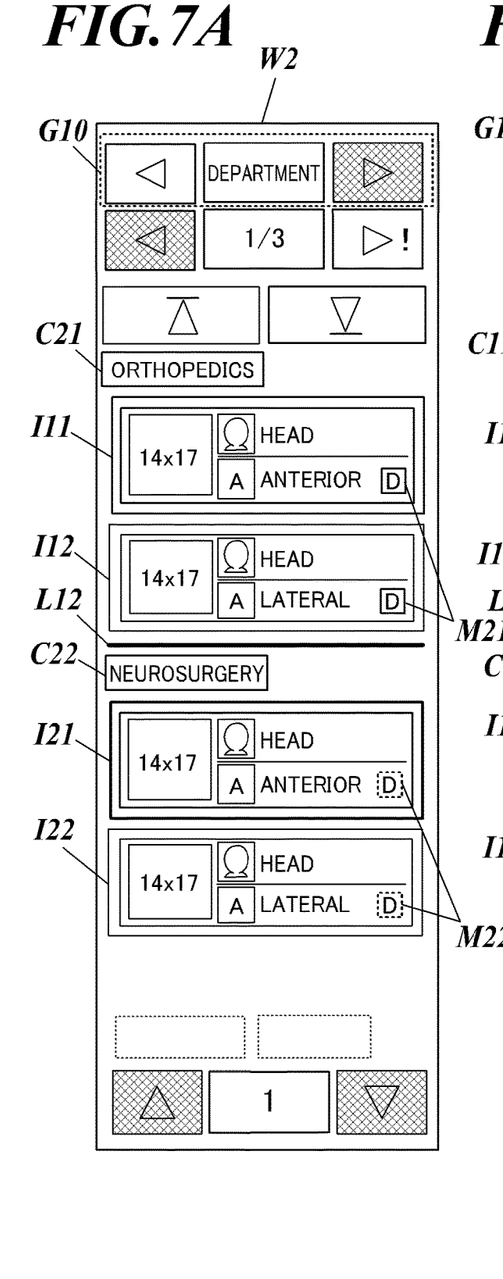
FIGS. 7A, 7B show examples of how to display the list when duplicate imaging items are present.
Figure 7B:
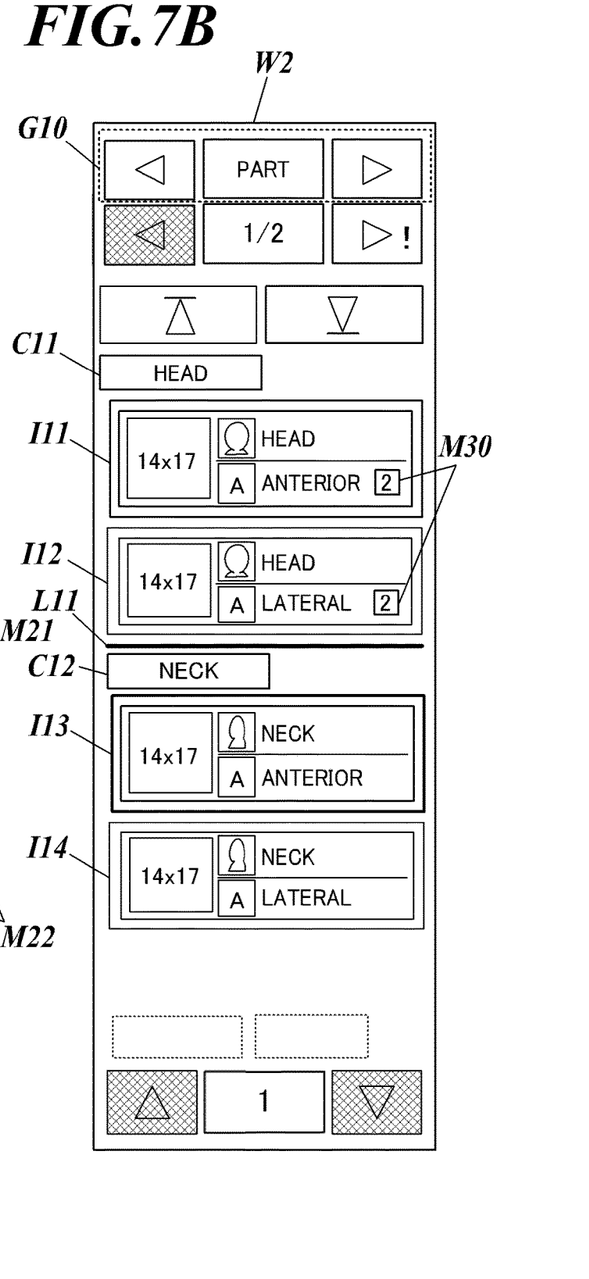

FIGS. 7A, 7B show examples of the list section W2 when duplicate imaging items are present.

In FIG. 7A, the categorization criterion is set to medical departments, and the categories include imaging items having the same imaging part and the same imaging conditions. These imaging items are displayed in the respective categories separated by the separating line L12. In FIG. 7A, the imaging item I11 of the orthopedics department and the imaging item I21 of the neurosurgery department have the same imaging part and the same imaging conditions. Further, the imaging item I12 and the imaging item I22 have the same imaging part.

In displaying these duplicate imaging items, the duplicate imaging items may have icons M21, M22 indicating that the set imaging contents are duplicate. The icon M21 for the first duplicate imaging items in the display order may be distinctive from the icon M22 for the other duplicate imaging items, or may be the same as the icon M22. Herein, the icon M21 is a solid-line frame, and the icon M22 is a dashed-line frame. When any of the duplicate imaging items is selected and radiography is performed for the selected imaging item, all the duplicate imaging items may be set as having been done.

FIG. 7B shows a case where the categorization criterion is set to imaging parts, as with FIG. 6A. In the case, the imaging items having the same imaging condition may be grouped and displayed as one. The imaging items I11, I12, each of which includes grouped imaging items, may be displayed along with icons M30 that indicate that the imaging items are grouped. Each icon M30 shows "2" as the number of duplicate imaging items as an example but not limitation. The grouped imaging items may be displayed individually when the operation receiver 113 receives a certain input operation.

Figure 8:
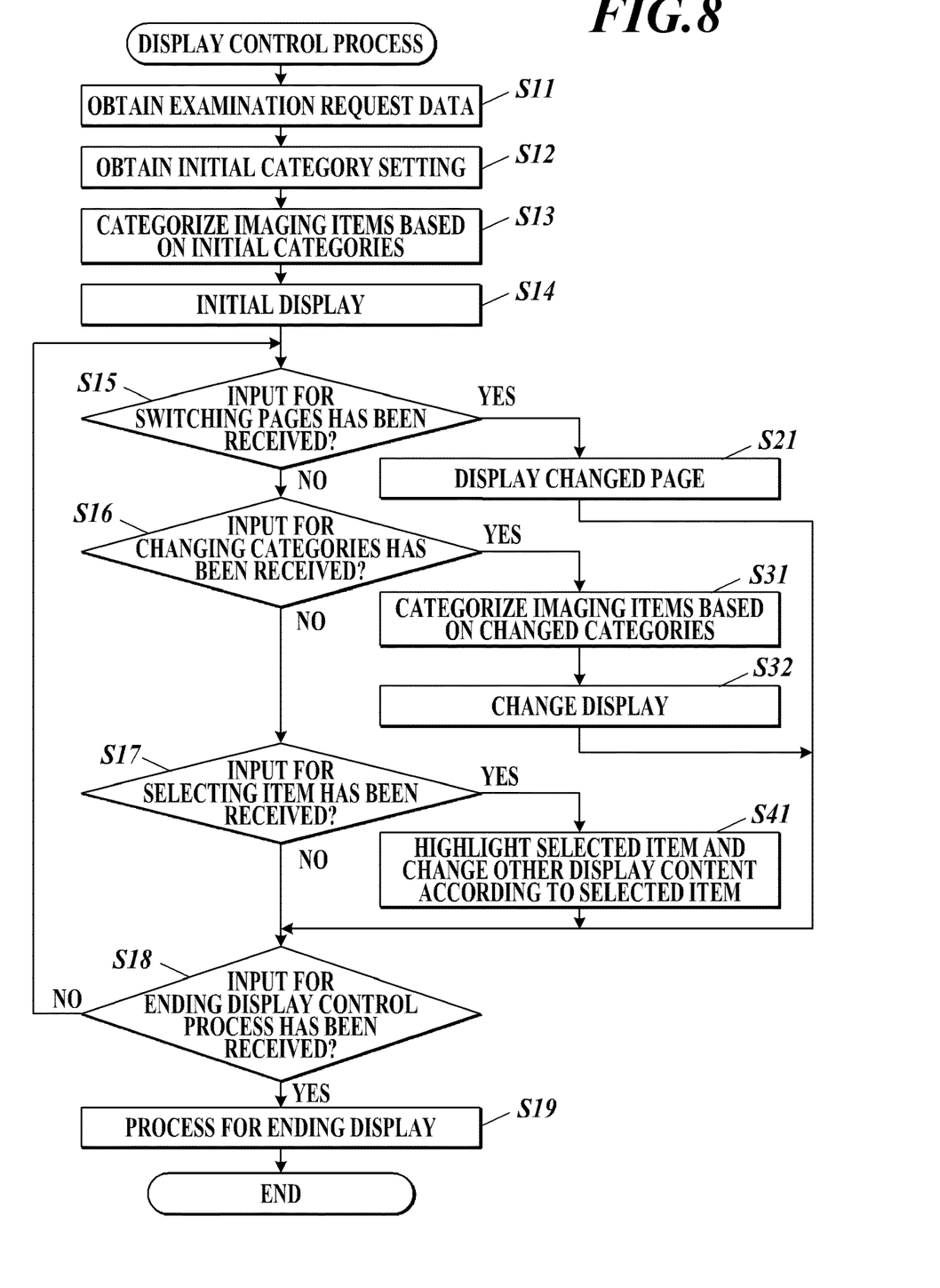
FIG. 8 is a flowchart of a display control process that is performed by the radiography control apparatus for controlling the radiography control screen.

FIG. 8 is a flowchart of a display control process for controlling the radiography control screen. The display control process is performed by the controller 111 of the radiography control apparatus 110 in this embodiment.

The display control process starts when the radiography control apparatus 110 starts processing for controlling radiography. The processing for controlling radiography, processing of taken images, and processing for display may start separately when the radiography control apparatus 110 receives an input operation for controlling radiography. These kinds of processing may be controlled in a known way, and the description thereof is omitted.

When the display control process starts, the controller 111 (CPU 1111) obtains the content of examination request data that has been received (Step S11). The controller 111 obtains a list of categories in the initial categorization criterion that is set beforehand and used for initially separating the imaging items (Step S12). The controller 111 categorizes all the imaging items of the obtained examination request data into the initial categories (Step S13). The controller 111 determines the display order of the categories and determines the display contents. The display order of the categories and/or the display order of imaging items in each category may be determined, for example, according to a predetermined order so as to minimize time and effort for radiography. Based on the determined display contents, the controller 111 causes the display 114 to perform initial display of the list section W2 (Step S14: item displaying step, item displaying unit).

The controller 111 determines whether or not the operation receiver 113 has received an input operation for switching pages to be displayed (Step S15). When determining that the input operation for switching pages has been received (Step S15: YES), the controller 111 changes the content of the list section W2 of the display 114 according to generated data on the page to be displayed (Step S21). The controller 111 then proceeds to Step S18.

When determining that an input operation for switching pages has not been received (Step S15: NO), the controller 111 determines whether or not the operation receiver 113 has received an input operation for changing the categorization criterion (Step S16). When determining that an input operation for changing the categorization criterion has been received (Step S16: YES), the controller 111 categorizes all the obtained imaging items based on categories of the changed categorization criterion (Step S31). The controller 111 determines the display order of the categories and determines the display contents. On the basis of the determined display contents, the controller 111 changes the display contents of the list section W2 (Step S32). The controller 111 then proceeds to Step S18.

When determining that an input operation for changing the categorization criterion has not been received (Step S16: NO), the controller 111 determines whether or not an input operation for selecting any of the imaging items has been received (Step S17). When determining that an input operation for selecting any of the imaging items has been received (Step S17: YES), the controller 111 highlights the selected imaging item. The controller 111 also changes the display contents of the preview section W1 and the setting section W3 according to the selected imaging item (Step S41). When the selected imaging item is not displayed in the list section W2 as described above, the controller 111 may change the display contents of the list section W2 so as to display the category that includes the selected imaging item. The controller 111 then proceeds to Step S18.

When determining that an input operation for selecting any of the imaging items has not been received (Step S17: NO), the controller 111 proceeds to Step S18. After proceeding to Step S18 from any of the Steps S18, S21, S32, and S41, the controller 111 determines whether or not the operation receiver 113 has received an input operation on an instruction to end the process of controlling radiography. When determining that an input operation on an instruction to end the process of controlling radiography has not been received (Step S18: NO), the controller 111 returns to Step S15. When determining that an input operation on an instruction to end the process of controlling radiography has been received (Step S18: YES), the controller 111 performs a process to end the display for controlling radiography on the display screen 1141 (Step S19) and ends the display control process.

As described above, the radiography control apparatus 110 in this embodiment includes the display 114 that includes the display screen 1141 and the controller 111. In causing the display screen 1141 to display a list of information on an examination that is set for a patient and that relates to taking a radiographic image, the controller 111 causes the display screen 1141 to display, in a display area (list section W2), imaging items that are included in the examination and categorized into categories based on a set categorization criterion, separating the imaging items by the category.

By grouping and displaying multiple examinations of a single patient, the radiography control apparatus 110 effectively restrains increase of work or burdens on examiners and patients. More specifically, the radiography control apparatus 110 avoids performing radiography several times that can be performed together and avoids moving back and forth between image-taking apparatuses or between imaging parts. Further, by displaying multiple imaging items on a category basis, the radiography control apparatus 110 allows a user (e.g., examiner) to view examination information (e.g., content of each examination) more efficiently and securely.

Furthermore, the radiography control apparatus 110 further includes the operation receiver 113. The controller 111 sets the categorization criterion according to an input operation received by the operation receiver 113 and causes the display screen 1141 to display the imaging items in the list section W2. The categorization criterion are thus changeable by input operations, and imaging items are separated and arranged to be easily seen according to the contents that the user (e.g., examiner) desires to check. This improves working efficiency of the user.

Furthermore, the controller 111 causes the display screen 1141 to display the imaging items that belong to different categories such that the imaging items are separated in different subareas. The controller 111 thus sets subareas in the list section W2 in listing imaging items. This allows the user (e.g., radiographer) to easily view the imaging items.

Alternatively, the controller 111 may cause the display screen 1141 to display the imaging items that belong to different categories such that the imaging items are separated by a separating icon, such as a predetermined separating line, in the list section W2. Such a simple separation also allows the user to easily distinguish the categories.

Furthermore, the controller 111 causes the display screen 1141 to display icons C1, C2 that indicate the categories in respective display regions into which the imaging items are separated. This allows the user to easily recognize which categorization criterion is currently used and to which category each imaging item belongs.

Furthermore, when multiple imaging items are set individually and have an identical content and belong to an identical category, the controller 111 causes the display screen 1141 to display one of the imaging items in the identical category. The imaging items having the same imaging part and the same imaging conditions can be altogether done by one time of radiography. The controller 111 displays such imaging items as one group. This simplifies display contents and allows the user to easily grasp how many times radiography is to be performed.

Furthermore, when radiography is performed for any of the imaging items having the identical content, the controller 111 determines that radiography has been performed for all the imaging items having the identical content. More specifically, after one time of imaging, the imaging items having the same imaging part and the same imaging conditions are displayed as having been done. This reduces work of the user.

Furthermore, in displaying all the imaging items having the identical content, the controller 111 causes the display screen 1141 to display an indication that indicates that the imaging items having the identical content are set to have duplicate imaging contents. The imaging items having the same imaging content may be displayed in multiple categories according to categorization criteria. In such a case, the imaging items are displayed such that the user (e.g., radiographer) can recognize the duplicate imaging items. The user can easily recognize under which imaging conditions radiography is to be performed and perform radiography efficiently.

Furthermore, the controller 111 switches the display contents of the list section W2 by categories. When there are large number of imaging items to be displayed in the list section W2 with respect to the display area, the imaging items can be appropriately separated for display.

Furthermore, in switching the display contents of the list section W2, the controller 111 causes the display screen 1141 to display the icons P2, P3 in the list section W2. The icons P2, P3 are for switching the currently displayed content to the content of not-displayed categories. When there are undone imaging items that are not displayed on the list section W2 and for which radiography has not been performed yet, the controller 111 causes the display screen 1141 to display the notification icons N1, N2, N6 in association with the icons P2, P3 for switching the currently displayed content to the content of the not-displayed categories that include the undone imaging items. Switching the display contents may be performed multiple times when the display contents are switched in order. With these icons, the user can avoid overlooking an undone imaging item(s) on several pages of the list and avoid failing to perform radiography.

Furthermore, the radiography system 100 in this embodiment includes the radiography control apparatus 110 and the radiographic-image taking apparatus 150 that takes radiographic images. The radiography control apparatus 110 in this embodiment controls the imaging operation of the radiographic-image taking apparatus 150, so that radiographic images are taken more efficiently and properly.

Furthermore, the display control method in this embodiment is for displaying, on the display 114, information on an examination that relates to taking a radiographic image. The method includes the item displaying step. The item displaying step is, in causing the display screen 1141 of the display 114 to display a list of the information on the examination that is set for a patient, causing the display screen 1141 to display, in the list section W2, imaging items that are included in the examination and categorized into categories based on a set categorization criterion such that the imaging items are separated by the category.

Thus, contents of examinations for a single patient are displayed as a group, and the imaging items are separately displayed by categories. This allows the user (e.g., examiner) to more efficiently and securely view examination information, such as examination contents.

Furthermore, the program 1121 in this embodiment may be installed on a computer that is used as the radiography control apparatus 110 and may be executed by the controller 111 (CPU 1111). The radiography control apparatus 110 can easily and efficiently control radiography performed by the radiographic-image taking apparatus 150, without a specific hardware structure.

The above embodiment does not limit the present invention and can be variously modified. For example, although the categories are distinguished by a separating line or a borderline in the above embodiment, the categories may be simply distinguished by a space if an enough display area is present. The categories may also be distinguished only by the icons at the top of the respective categories. Further, the categories may be clarified by numbers instead of or in addition to illustrated separating icons. For example, each category may have a specific number or a symbol to clarify imaging items as "1-1", "1-2", and "2-1".

Further, although in the above embodiment the categories are separated by a level and solid straight line, the separating line may be of any visually recognizable shape.

Further, although in the above embodiment the subareas are defined by different background colors or by borderlines, the combination of colors and borderlines is also applicable. Also, the shape of the borderlines is not limited.

Further, the categorization criterion may not be changed in response to operations by the user. The categorization criterion may be automatically changed so as to accord with the imaging order after radiography starts.

Further, the storage 112, the operation receiver 113, and the display 114 may be external devices that are appropriately attached to a computer.

Further, the above embodiment displays a notification that indicates presence of a not-displayed undone imaging item on the icon for switching display contents. However, the notification may not be on the switching icon but may be displayed separately from the switching icon. Further, the notification may be an icon that specifies which page includes an undone imaging item. The notification may further specify the number of undone imaging items in addition to presence of undone imaging items.

Further, the position and shape of the list section W2 and the contents, shapes, and arrangements of the imaging items in the list section W2 are not limited to the above embodiment.

Further, although in the above description categories and imaging items are sorted in the display order according to setting before being displayed, the sorting may not be performed. Further, the user may change the display order of categories and/or imaging items through the drag operation, for example. When the display order is different from the imaging order, the next imaging item in the imaging order may be distinguishably highlighted or colored.

Further, in the above description, the storage 112 includes an auxiliary storage device(s), such as a flash memory and/or a HDD, as a computer-readable storage medium that stores the program 1121 regarding the processing operation of the controller 111 in the present invention. However, the storage medium is not limited thereto. As other computer readable storage media, a portable storage medium, such as a CD-ROM or a DVD disk, may also be used. Further, a carrier wave can be used as a medium that provides data of the program according to the present invention via a communication line.

The detailed configuration and contents and procedure of processing operations in the above embodiment can be appropriately modified without departing from the scope of the present invention. The scope of the present invention includes the scope of the present invention described in the scope of claims and the scope of their equivalents.

What is claimed is:

1. A radiography control apparatus, comprising:
   a display that includes a display screen;
   an operation receiver configured to receive a first input operation; and
   a hardware processor, wherein the hardware processor causes the display screen to display a list of information on an examination that is set for a patient and that relates to taking a radiographic image,
   categorizes each imaging item of multiple imaging items that are included in the examination into different categories based on a set categorization criterion, and
   causes the display screen to display, in a display area, the different categories,
   wherein each category of the different categories includes at least one imaging item of the multiple imaging items, and for each category of the different categories, the hardware processor determines whether to spread and display the at least one imaging item of the multiple imaging items of the each category based on the first input operation.

2. The radiography control apparatus according to claim 1, wherein
   the hardware processor causes the display screen to display the different categories such that the different categories are separated by a predetermined separating icon in the display area.

3. The radiography control apparatus according to claim 1, wherein
   the hardware processor causes the display screen to display indications that indicate the different categories in respective display regions into which the imaging items are separated.

4. The radiography control apparatus according to claim 1, wherein
   the multiple imaging items include plural imaging items that are set individually and that have an identical content and that belong to an identical category, and
   the hardware processor causes the display screen to display one of the imaging items of the plural imaging items in the identical category.

5. The radiography control apparatus according to claim 1, wherein the hardware processor switches a display content of the display area by the category.

6. A radiography system comprising:
   the radiography control apparatus according to claim 1; and
   a radiographic-image taking apparatus that takes the radiographic image.

7. The radiography control apparatus according to claim 1, wherein the hardware processor, in response to a second user input on the operation receiver, switches the set categorization criterion to a second categorization criterion and displays the imaging items in further categories based on the second categorization criterion, separating the imaging items by the further categories.

8. The radiography control apparatus according to claim 1, wherein the different categories are placed in separate regions of the display area having different background colors.

9. The radiography control apparatus according to claim 3, wherein each of the indications indicates an imaging part.

10. The radiography control apparatus according to claim 4, wherein in response to radiography being performed for any of the plural imaging items having the identical content, the hardware processor determines that radiography has been performed for all the plural imaging items having the identical content.

11. The radiography control apparatus according to claim 4, wherein, in displaying all the plural imaging items having the identical content, the hardware processor causes the display screen to display an indication that indicates that the plural imaging items having the identical content are set to have duplicate imaging contents.

12. The radiography control apparatus according to claim 5,
wherein, in switching the display content of the display area, the hardware processor causes the display screen to display, in the display area, a switching icon for switching the display content to a display content of a not-displayed category among the categories, and
in response to the not-displayed category including an imaging item for which radiography has not been performed, causes the display screen to display a predetermined indication that is associated with the switching icon.

13. The radiography control apparatus according to claim 12, wherein the hardware processor further displays a number of undone imaging items on the display.

14. A display control method for displaying, on a display, information on an examination that relates to taking a radiographic image, the method comprising:
categorizing each imaging item of multiple imaging items that are included in the examination into different categories based on a set categorization criterion,
displaying a list of the information on the examination that is set for a patient on a display screen, the step of displaying the list of the information on the examination including displaying the different categories on the display screen in a display area,
wherein each category of the different categories includes at least one imaging item of the multiple imaging items, and determining, for each category of the different categories, whether to spread and display the at least one imaging item of the multiple imaging items of each category based on a first input operation received by an operation receiver.

15. A non-transitory computer readable storage medium storing a program that causes a computer including a display screen to: display a list of information on the display screen on an examination that is set for a patient and that relates to taking a radiographic image,
categorize each imaging item of multiple imaging items that are included in the examination into different categories based on a set categorization criterion,
displays, in a display area, the different categories
wherein each category of the different categories includes at least one imaging item of the multiple imaging items, and determine, for each category of the different categories, whether to spread and display the at least one imaging item of the multiple imaging items of each category based on a first input operation received by an operation receiver.

* * * * *